(12) United States Patent
Doyle

(10) Patent No.: US 7,100,891 B2
(45) Date of Patent: Sep. 5, 2006

(54) VALVED MALE LUER WITH VACUUM FEATURE

(75) Inventor: Mark C. Doyle, San Diego, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 74 days.

(21) Appl. No.: 10/858,719

(22) Filed: Jun. 2, 2004

(65) Prior Publication Data

US 2004/0217315 A1    Nov. 4, 2004

Related U.S. Application Data

(63) Continuation of application No. 09/927,109, filed on Aug. 10, 2001, now Pat. No. 6,745,998.

(51) Int. Cl.
*F16K 51/00*  (2006.01)
*F16L 29/00*  (2006.01)
*F16L 37/28*  (2006.01)

(52) U.S. Cl. ............... 251/149.6; 604/241; 251/149.3; 251/149.6

(58) Field of Classification Search ............ 251/149.1, 251/149.3, 149.4, 149.6; 604/167.02, 167.03, 604/167.04, 200, 201, 246, 249, 905
See application file for complete search history.

(56) References Cited

U.S. PATENT DOCUMENTS

| | | | |
|---|---|---|---|
| 2,931,668 A | 4/1960 | Baley | |
| 2,968,497 A | 1/1961 | Treleman | |
| 4,233,982 A | 11/1980 | Bauer et al. | |
| 4,245,635 A | 1/1981 | Kontos | |
| 4,379,458 A | 4/1983 | Bauer et al. | |
| 4,862,913 A | 9/1989 | Wildfang | |
| 5,065,783 A | 11/1991 | Ogle, II | |
| 5,098,385 A | 3/1992 | Walsh | |
| 5,203,775 A | 4/1993 | Frank et al. | |
| 5,211,634 A | 5/1993 | Vaillancourt | |
| 5,334,159 A | 8/1994 | Turkel | |
| 5,380,306 A | 1/1995 | Brinon | |
| 5,397,314 A | 3/1995 | Farley et al. | |
| 5,405,323 A | 4/1995 | Rogers et al. | |
| 5,405,333 A | 4/1995 | Richmond | |
| 5,492,147 A | 2/1996 | Challender et al. | |
| 5,514,117 A | 5/1996 | Lynn | |
| 5,520,665 A | 5/1996 | Fleetwood | |
| 5,540,661 A | 7/1996 | Tomisaka et al. | |
| 5,549,566 A | 8/1996 | Elias et al. | |
| 5,575,769 A | 11/1996 | Vaillancourt | |
| 5,578,059 A | 11/1996 | Patzer | |
| 5,584,819 A | 12/1996 | Kopfer | |
| 5,645,538 A | 7/1997 | Richmond | |
| 5,676,346 A | 10/1997 | Leinsing | |

(Continued)

*Primary Examiner*—Edward K. Look
*Assistant Examiner*—John K. Fristoe, Jr.
(74) *Attorney, Agent, or Firm*—Fulwider Patton LLP

(57) ABSTRACT

A male luer connector device that attaches to any standard female luer valve to open a flow channel between the two luers. The male luer is comprised of a tubular housing element, a resilient member contained within the housing and extending within an inner tubular portion defined in the housing, a resilient member that extends within the inner tubular portion of the housing, and a valve member attached to the resilient member that seals the tubular portion. When the male luer is engaged with any standard female luer, a female luer connector device drives the resilient member of the male luer into a compressed position to open the forward end of the male luer and permit liquid flow between the luers.

5 Claims, 7 Drawing Sheets

U.S. PATENT DOCUMENTS

| | | |
|---|---|---|
| 5,738,144 A | 4/1998 | Rogers |
| RE35,841 E | 7/1998 | Frank et al. |
| 5,782,816 A | 7/1998 | Werschmidt et al. |
| 5,806,831 A | 9/1998 | Paradis |
| 5,839,715 A | 11/1998 | Leinsing |
| 5,848,994 A | 12/1998 | Richmond |
| 6,068,011 A | 5/2000 | Paradis |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,206,860 B1 | 3/2001 | Richmond |
| 6,299,132 B1 | 10/2001 | Weinheimer et al. |
| 6,485,472 B1 | 11/2002 | Richmond |
| 2003/0060779 A1 | 3/2004 | Richmond |

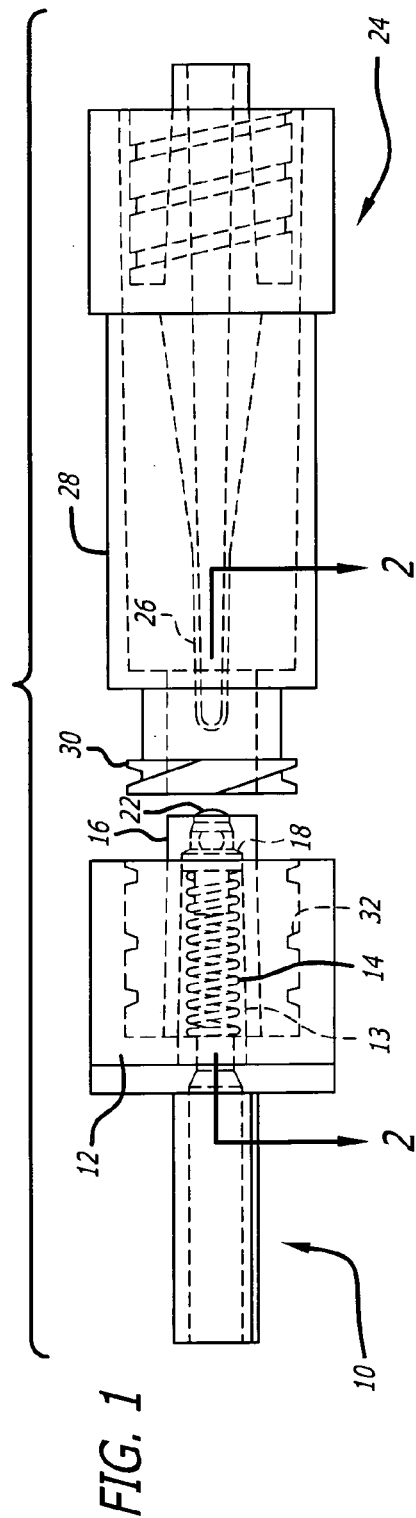
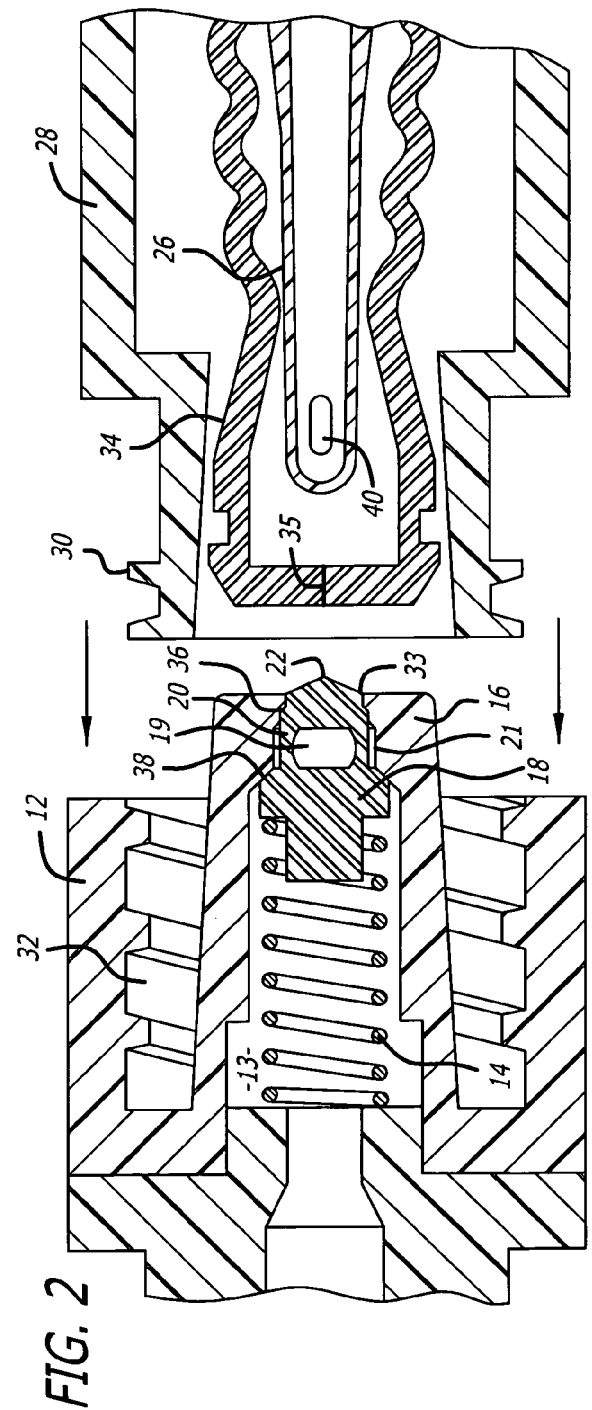
FIG. 1
FIG. 2

VALVED MALE LUER WITH VACUUM FEATURE

This application is a continuation of application Ser. No. 09/927,109, filed on Aug. 10, 2001 now U.S. Pat. No. 6,745,998.

BACKGROUND OF THE INVENTION

This invention relates to an improved male luer connector device that attaches to a female luer valve to open a flow channel through the male luer. Once the engagement of the luers has been established, these valves are used to make connections in hospitals for intravenous (IV) devices in order to be used in medical liquid flow applications.

Luer devices are used in particular in a variety of medical applications where there is a desire to interconnect together male and female connector parts onto tubing material that is connected to an IV. The most common types of IV fluid exchanges use a syringe fitted with a nozzle that is designed to be received into a corresponding receiver attached to the IV device. The receiver often has a hollow tubular cannula or post that routes fluid into a line inserted into the IV extending into the patient's veins.

Typical luer connections utilize a male luer connector that is inserted into a female luer connector. The male luer connector is threaded onto corresponding threads of the female luer connector to engage the two so that fluid may be passed between them without escaping or leaking from the connection. Because these connections are subject to coming loose or disengaging, there is always a possibility that fluid being passed within these tubes can escape. When using hazardous drugs, such as those used for chemotherapy treatments, the possibility of escaping fluids can be a dangerous problem. Additionally, even if the fluid does not leak when the connectors are engaged, once they are disengaged, the residual amount of fluid remaining on the tip of the connectors can still be harmful. While this amount may be less than an amount escaping from the connectors, it can still be significant enough to cause harm to any person exposed.

Therefore, there is a need for a luer connection that securely contains the fluid materials included therein when luers are engaged to one another. There is also a need for a luer connection that seals off the male luer connector in a male-female connection so that users of the connector are protected from hazardous drugs that remain on the luer tip surface when disengaged.

SUMMARY OF THE INVENTION

It is an object of the present invention to provide a new and improved male luer connector device for engagement with a female luer valve for connection to an IV or other fluid-type connections.

According to one aspect of the present invention, a male luer connector device is provided for establishing a connection with a corresponding core rod type female luer valve. The device comprises a housing, an inner chamber, a resilient member, and a valve member. The housing has an outer tubular portion and an inner tubular portion and first and second necked areas and the valve member has a tip that seals the forward end of the inner tubular portion. The resilient member can be elastically displaced and extends within the inner tubular portion of the housing.

The male luer is inserted into a corresponding core rod or cannula female luer and the two are engaged. When the female luer engages with the male luer, the core rod within the female luer valve pushes first against the tip of the male luer. The tip then moves and collapses the valve member at the first necked area. Further engagement continues to move the valve member and then collapses the resilient member at the second necked area. Once the luers are entirely in the engaged position, fluid may flow between the luers and enter or exit the female luer via an inlet port. If it is desired, the male luer valve does not have to be contained within a housing element. Instead, it may be self contained or additionally, those skilled in the art will recognize that the male luer valve can be contained within other enclosures.

According to another aspect of the present invention, a male luer connector device is provided that comprises a resilient member, a inner chamber, and a valve member. This embodiment functions identically to the prior embodiment with the exception that the valve member is either integrally formed with the resilient member or can be abutting the resilient member. The resilient member can be formed of an elastomeric material or can be a spring formed of many different materials. The inner chamber is then sealed off by the integrally formed member. When an appropriate female luer valve is engaged with the male luer, the integrally formed member collapses in order to permit liquid flow between the two luers. If desired, this embodiment may alternatively contain a housing.

In a further embodiment, a male luer is described that can work with a female luer that does not contain a cannula or post. This luer comprises a housing, a first tubular member, a resilient member, a valve member, and a slidable sleeve member. The housing has an outer tubular wall and a first tubular member which extends co-axially within the housing. The first tubular member has at least one axially extending slot and a forward end having a valve seat. The valve member is located at the end of the resilient member for sealing engagement of the valve seat. The resilient member has at least one guide portion that extends radially outwardly through the axial slot. The sleeve member is slidably mounted over the first tubular member and the outer tubular wall so that the sleeve traps the guide portion. When the female luer is engaged to the male luer, the housing of the female luer engages the sleeve and slides it rearwardly into the male luer housing. This pushes the resilient member and the valve member rearwardly into a retracted position to allow liquid flow between the two luers. Once again in this embodiment, the housing element does not have to be present. Instead, the male luer valve may be self contained or contained within other types of enclosures.

The configurations of the present invention described herein are advantageous for many reasons. When the male luer is mated or disengaged with an appropriate female luer valve, the male connector seals off to protect any user from exposure to potentially hazardous fluids. The valve contained on the end of the male luer is self-closing so that it ensures that minimal amounts of fluid remain on any exposed surface of the luer. This advantage helps ensure hazardous drugs, such as those used in chemotherapy treatments, do not remain on the luer. Also, bodily fluids, such as blood, do not remain on the luer in order to minimize exposure to potentially diseased blood. The valve design allows either mutual swabbing or one-sided swabbing because there are minimal crevices on the luer and the tip member is substantially flush. Additionally, in one embodiment, the configuration of the male luer provides another advantage in that it creates a vacuum effect on the tip of the luer when the male and female luer are disengaged. This vacuum tip feature acts to minimize residual fluid on any surface and therefore minimizes all types of exposure.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a side view of the two components of the male to female luer connection of the luer fitting;

FIG. 2 is an enlarged sectional view taken on line 2—2 of FIG. 1;

DETAILED DESCRIPTION OF THE DRAWINGS

Figure 3:
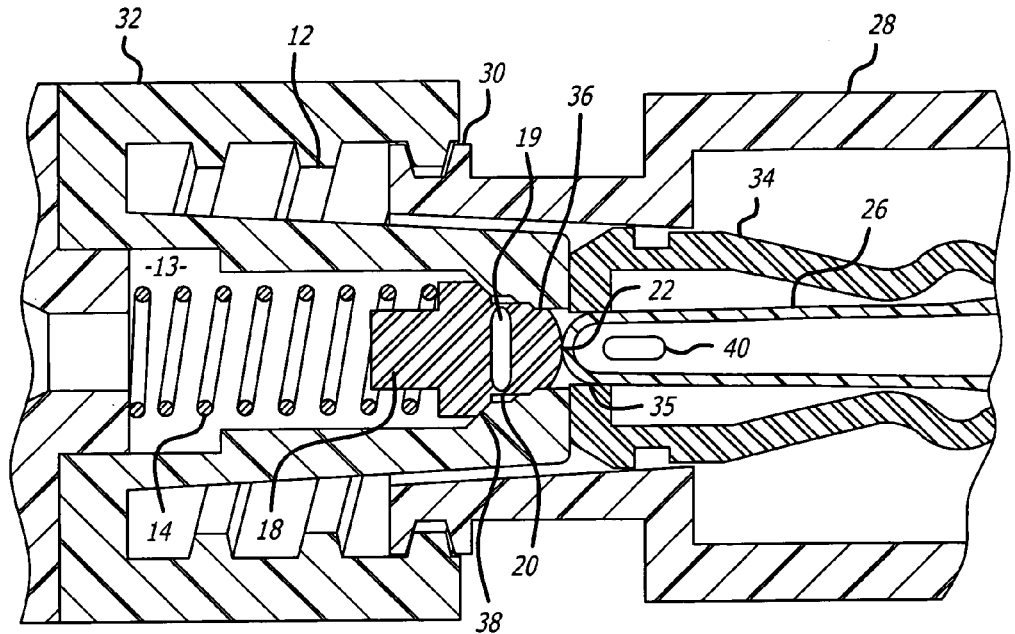
FIG. 3 is a view similar to FIG. 2, with the components partially engaged.

FIG. 1 is a side view of the two components of the male to female luer connection of the luer fitting. The fitting is comprised of a male luer 10 that is intended to engage with a female luer that has an existing flush top female luer valve. The female luer 24 is not limited to a particular type but an exemplar luer is illustrated here. The female luer illustrated here is one where the valve shuts off. This female luer 24 contains a housing element 28 with a cannula or post 26. On the outer surface of the forward end of the housing 28 there are threads 30 that permit engagement of the female luer 24 with the male luer 10. In this embodiment the male luer 10 is comprised of a housing element 12. The inner wall of the housing 12 contains threads 32 that engage the complimentary threads 30 of the female luer connector. Housing 12 has an inner tubular portion 16 of reduced diameter that projects forwardly that has a first necked area 36 and a second necked area 38 (See FIG. 2). The inner tubular portion defines an internal chamber 13 with a forward opening 33 (See FIG. 2). A valve member 18 is biased into an extended position sealing opening 33 by resilient member or spring 14. Spring 14 acts between distal end of chamber 13 and valve member 18. Valve member 18 includes a resilient portion 20 and a forward tip member 22. FIG. 1 illustrates the two luers 10, 24 in the unengaged position. Other types of female luer valves that do not contain a cannula or post. By way of example, U.S. Pat. No. 5,676,346 by Leinsing and U.S. Pat. No. 5,782,816 by Werschmidt illustrate these types of luer valves.

FIGS. 2 to 5 illustrate the male luer 10 and the female luer 24 as they become engaged with one another. FIG. 2 illustrates the two luers 10, 24 when they are completely unengaged. The cannula or post 26 may have an opening 40 for entrance and exit of fluid between the two luers. Other duct systems (not shown) are possible and may be used. The cannula or post 26 is mounted in a chamber within a sleeve 34. This sleeve 34 can be made of rubber or any other suitable resilient material and serves as a valve member stopper. Sleeve 34 has a forward end opening 35 which is sealed shut in the unengaged position of FIG. 2. The male luer has a forward end that has a first necked area 36 and a second necked area 38 spaced rearwardly from the first necked area 36. FIG. 3 illustrates the male luer 10 beginning to be inserted into the female luer 24. Once the threads 30,32 begin to engage, the forward end 33 of housing 12 pushes the sleeve 34 back until the opening 35 is forced to open over the end of the cannula 26. The cannula or post 26 then comes into contact with the tip of valve member 18 and begins to push it rearwardly so that the cannula or post 26 displaces the valve element front section 22. This movement begins to separate the seal surface of the first necked area 36 from its seat. As the tip member 22 begins to be pushed back, the second resilient portion 20 is collapsed, compressing the valve element cavity 19. This unseals the first necked area 36 and displaces the liquid contained within the cavity 19. This displaced liquid flows temporarily into the female luer valve 24. As this pressure is applied, the valve member is compressed and pushed further inwardly into chamber 13.

Figure 4:
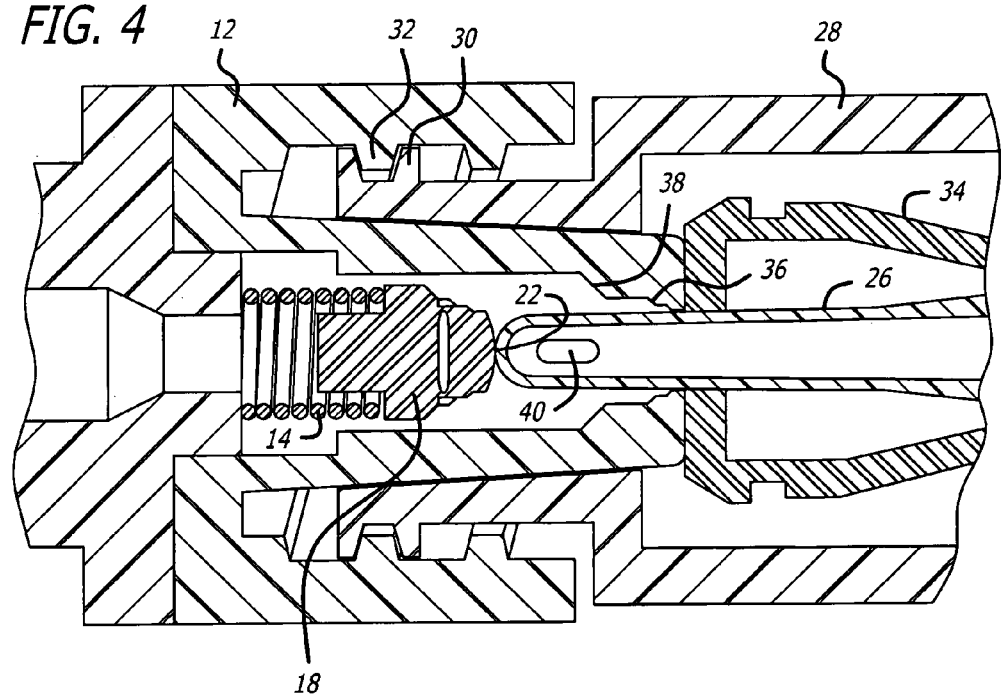
FIG. 4 is a view similar to FIG. 3, with the components fully engaged.

FIG. 4 illustrates the positioning of the luer members when the female 24 and male 10 luers have been even further engaged. The cannula or post 26 begins to push even more onto the tip member 22 and collapse the first resilient member 14 so that the second necked area 38 is unsealed. At this point, more liquid is displaced by the further insertion of the cannula or post into the vacuum section 21 of the male luer as indicated by the arrows in FIG. 4. The opening 40 on the cannula or post 26 permits fluid to pass into and out of the female luer 24. This displaced liquid creates the volume which will be refilled when the action is reversed.

Upon disconnection of the male luer 10 valve from the female luer valve 24, the volume of liquid that was displaced during the connection of the two valves is restored to the original positions, thus creating a relative vacuum. When the female luer 24 is removed from the male luer 10, the main seal created by the second necked area 38 makes contact with its seat. This isolates the vacuum section 21 from the upstream liquid. As the cannula or post 26 is withdrawn, cavity 19 is restored as resilient portion 20 resiles to its uncollapsed natural shape. As this restoration occurs, liquid is drawn into cavity 19. Because the second necked area 38 is closed, this liquid will be drawn from the interface between the male luer 10 and the female luer 24. This effect is enhanced by the volume represented by the cannula or post 26, which must be replaced as the cannula or post 26 is withdrawn. The relative vacuum created will attempt to draw liquid into the vacuum section until the seal surface of the first necked area 36 again contacts its seat.

Figure 5:
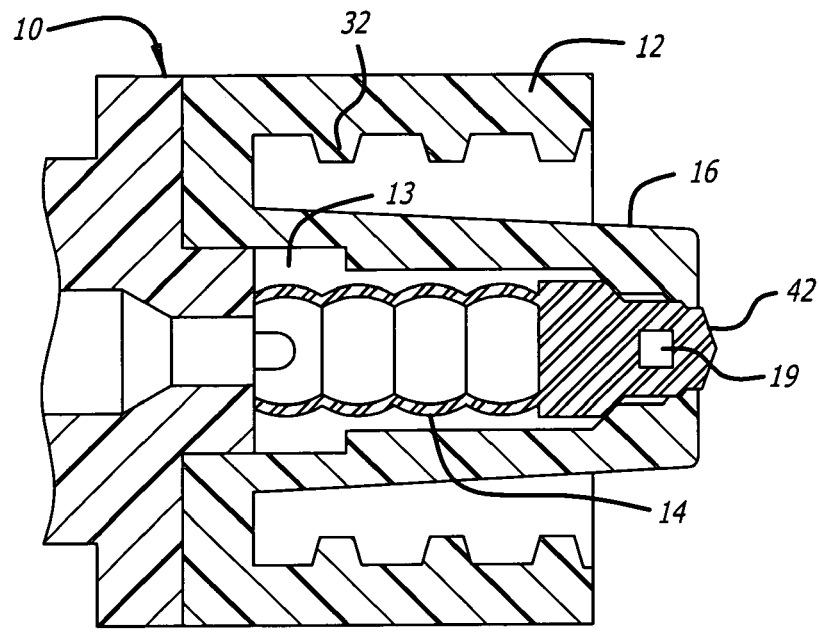
FIG. 5 is a view similar to a portion of FIG. 2, showing an alternative integrated spring member.

FIG. 5 illustrates the same type of dual stage valve as above only that it is formed with the spring 14 integrally connected to the valve member 42. The housing 12 contains the inner sleeve 16 and positioned inside of the inner sleeve 16 is an inner chamber 13. The function of this embodiment is the same as the previously described embodiments with the exception that the spring 14 can be comprised of elastomeric or other types of material that are integrally connected with the valve member 42.

Figure 6:
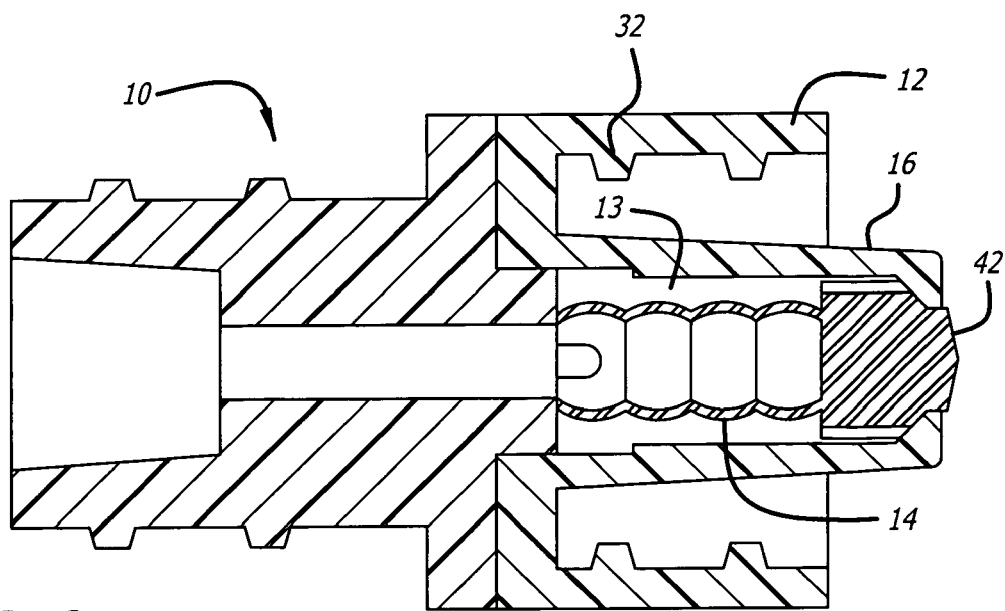
FIG. 6 is a view similar to FIG. 5, showing an alternative single stage valve.
Figure 7:
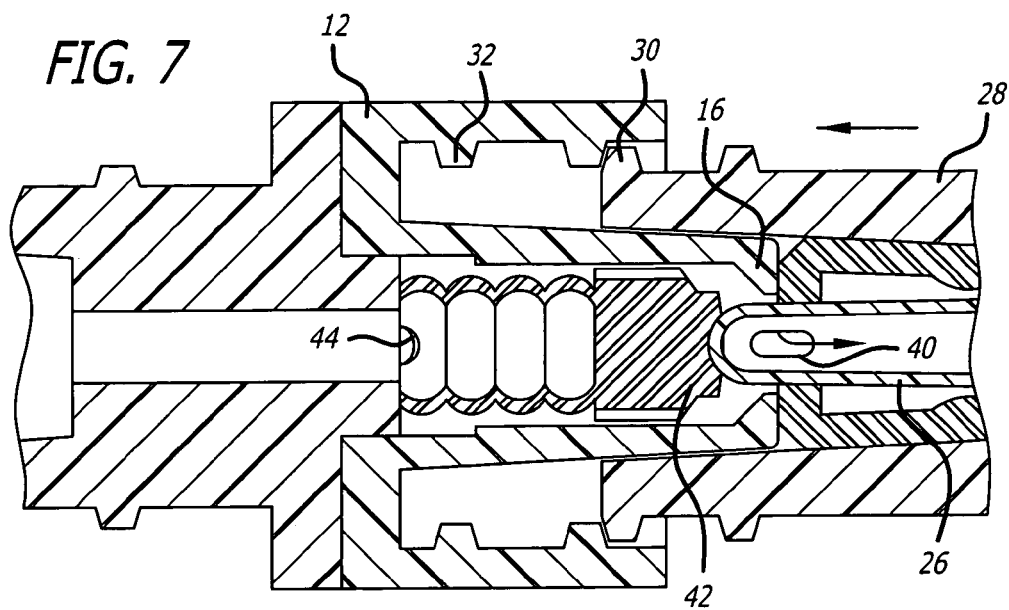
FIG. 7 is a view similar to FIG. 6, showing the valve opened.

FIGS. 6 and 7 illustrate a male luer according to another embodiment of the present invention. This apparatus is a single stage luer valve with an integral resilient member. In this embodiment, the male luer has a housing 12 with threads 32 on the inner wall of the housing for engagement to the complimentary threads on the female luer 30. The inner chamber 13 is sealed by a valve member 42 that is integrally formed with the resilient member and the tip. This new valve member 42 therefore functions as in the previous embodiment except that all members are formed in one piece, rather than including a separate resilient member. This embodiment demonstrates a single stage luer valve in that once the female luer engages with the valve member 42, the member 42 moves as a single piece rather than as several different pieces as described above. FIG. 7 illustrates the luer of FIG. 6 engaged with a female luer 24 and permitting fluid flow. Once the two luers 10, 24 are engaged, the cannula or post 26 of the female luer 24 collapses the valve member 42 and permits fluid flow via the opening 40 in the cannula or post 26 and also via an opening 44 in the rear end of the valve member 42.

Figure 8:
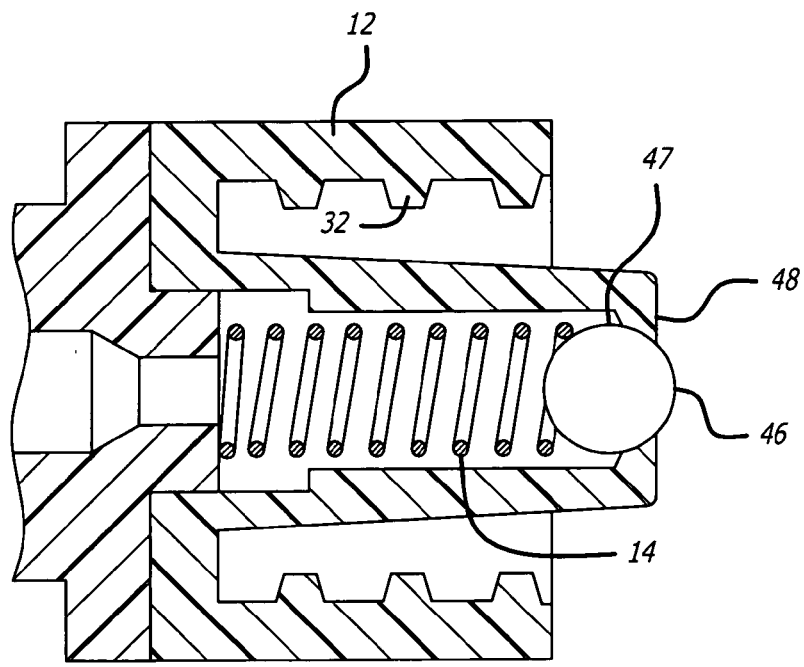
FIG. 8 is a view similar to FIG. 5, showing a ball type valve.

FIG. 8 illustrates another embodiment of the present invention. In this embodiment, the housing 12 of the male luer is similar to the previous embodiments. Additionally, contained within the inner sleeve 16 is a resilient member or spring 14. However, in this embodiment, the valve contained on the end of the resilient member is shown as a ball 46. This ball may be made of various types of materials as for example, elastomeric material. Additionally, the forward end opening of chamber 13 is exemplefied as a part-spherical seat 47 to accommodate for ball valve 46. Those skilled in the art will recognize that the valve contained on the end of the resilient member or spring 14 can be of a variety of shapes. However, the shape of the tip of the male luer 10 needs to be one that corresponds to the shape of the tip of the female luer 24.

Figure 9:
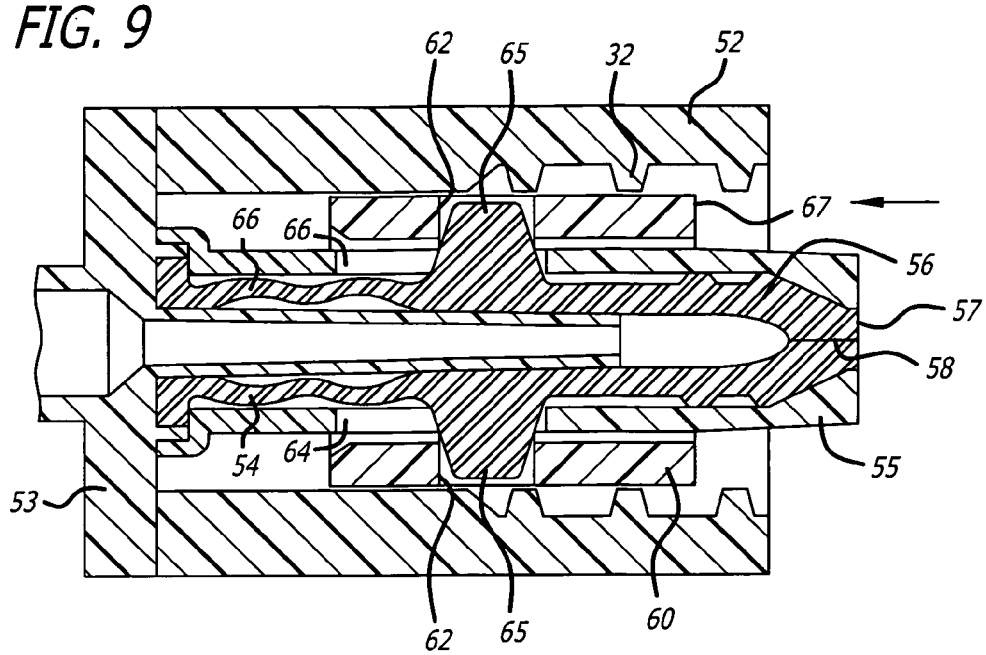
FIG. 9 is a sectional view showing an alternative slide actuated valve.
Figure 10:
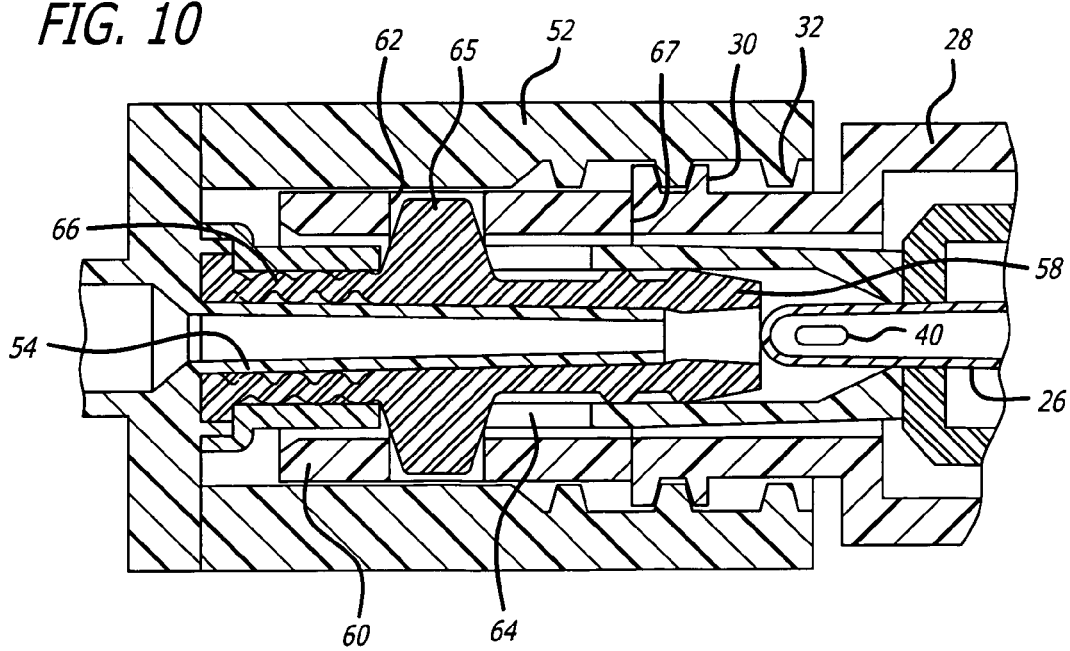
FIG. 10 is a view similar to FIG. 9, showing the valve opened.

FIGS. 9 and 10 illustrate a modified connector according to yet another embodiment of the present invention, in which a modified male luer 50 is releasably securable to the female luer 24 of the previous embodiments. Male luer 50 comprises a housing with a cylindrical outer wall 52 and an inner tubular support 54 which projects into the cylindrical housing from rear end 53 and extends along part of the length of the housing. Outer wall 52 has internal threads 32 for engaging the female luer threads 30 and a larger diameter than the inner support 54 which extends from the rear end 53 of the housing and projects out of the forward end of the housing. A resilient sleeve or bladder member 56 is secured between the tubular member 55 and support 54 at its rear end, and projects forwardly within tubular member 55 to its forward end opening 57. Bladder member 56 has a forward end opening 58 which is sealed shut by the inwardly tapered end portion of the tubular member 55 when in the extended, unconnected position of FIG. 9. The forward end portion 58 of bladder member 56 acts as a valve to seal the end opening 57 of the male luer in the position illustrated in FIG. 9.

Tubular member 55 of the male luer is of smaller diameter than the inner cylindrical wall 52 of the housing, to leave an annular gap between the member 55 and inner wall 52. A sliding sleeve 60 is slidably mounted over the tubular member 55 in this annular gap. Sleeve 60 has diametrically opposed openings 62, and the tubular member 55 has opposing elongate, axially extending slots 64. Oppositely directed wings or guide portions 65 on the inner bladder or sleeve member 56 project radially outwardly through the slots 64 and into the openings 62. Thus, when the sleeve is in the fully extended position of FIG. 9, it will pull the sliding sleeve forwardly into the illustrated position. The corrugated portion 66 of bladder member 56 acts as a spring to bias the forward end of the bladder member 56 and the sliding sleeve 60 into the extended position.

FIG. 10 illustrates a female luer 24 connected to male luer 50. As the forward end of the female luer housing is threaded into the cylindrical wall of the male housing, it will engage the forward end 67 of the sliding sleeve 60, urging the sleeve, and thus the bladder member 56, rearwardly and moving the forward end portion of the bladder member out of sealing engagement with the forward end opening of tubular member 55. This permits the forward end opening 58 to spring open, as indicated. At the same time, the forward end of tubular member 55 will force the sleeve 34 in the female luer rearwardly so that it passes over the end of cannula 26, which then extends into the open forward end of the tubular member. This allows fluid flow through the two luers, via the inner tubular support, open end 58 of the bladder member 56, and the openings 40 in the cannula 26. When the luers are disconnected, the compressed corrugated portion 66 of the bladder member 56 urges the forward end portion to move back into sealing engagement with the forward end of the tubular member 55, preventing any fluid leakage.

Figure 11:
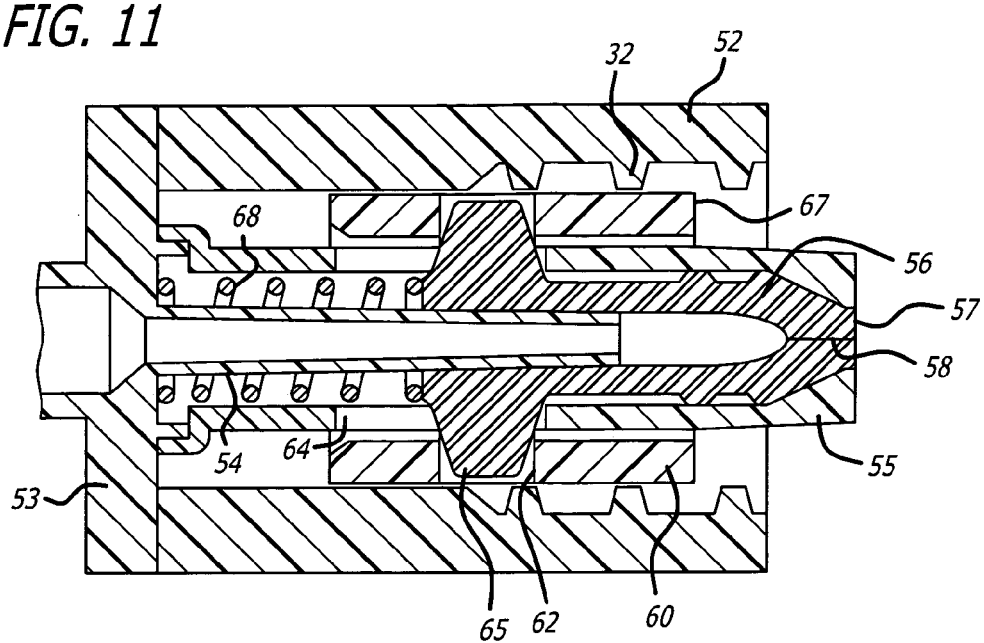
FIG. 11 is a view similar to FIG. 9, showing an alternative slide actuated valve.

FIG. 11 is a view similar to FIG. 9, showing an alternative slide actuated valve except that the resilient sleeve or bladder member 56 does not have a corrugated portion and instead has a separate spring member 68. The spring member 68 can any type as for example, those made of metal or elastomeric material. The function of the male luer valve is the same, it is merely the spring member 68 that replaces the previous corrugated member.

Figure 12:
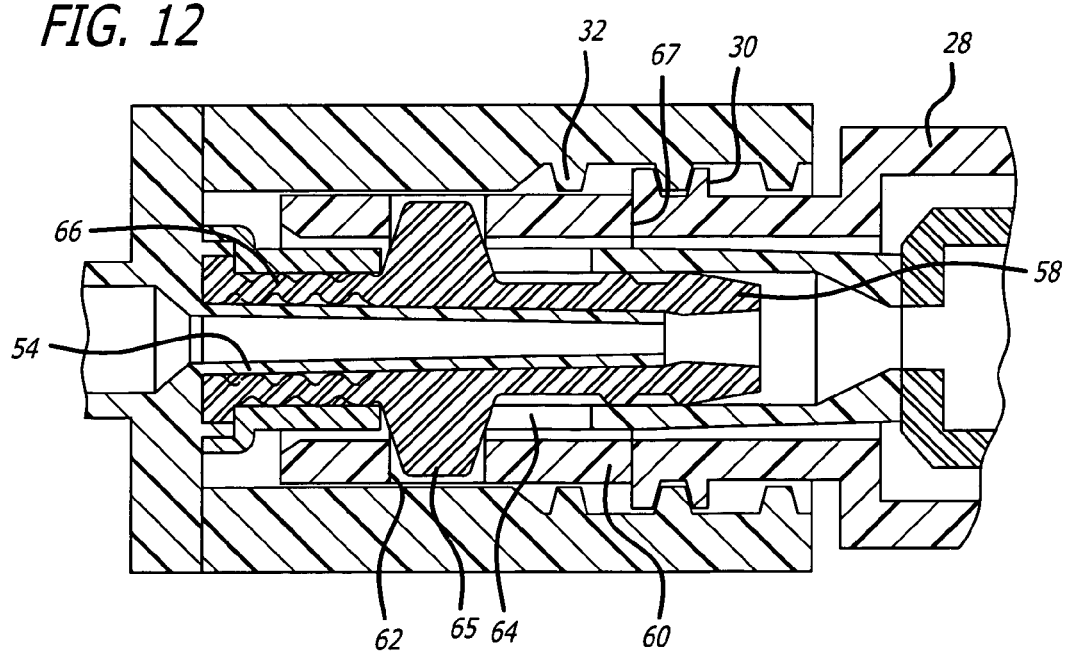
FIG. 12 is a view similar to FIG. 10, showing an alternative valve for use with a female luer valve that does not have a cannula or post.

FIG. 12 is a view similar to FIG. 10, showing an alternative valve for use with a female luer valve that does not have a cannula or post. The outer surface of the forward end of the housing 28 engages and compresses the forward end 67 of the sliding sleeve 60 of the male luer valve. As the forward end of the female luer valve housing 28 continues to further displace the sliding sleeve 60, the bladder member 56, continues to move rearwardly and moves the forward end portion of the bladder member out of sealing engagement with the forward end opening of the tubular member 55. This permits the forward end opening 58 to spring open. This allows fluid flow through the two luers, via the inner tubular support, open end 58 of the bladder member 56. Once the luers are disconnected, the sealing engagement as previously described once again occurs.

Figure 13:
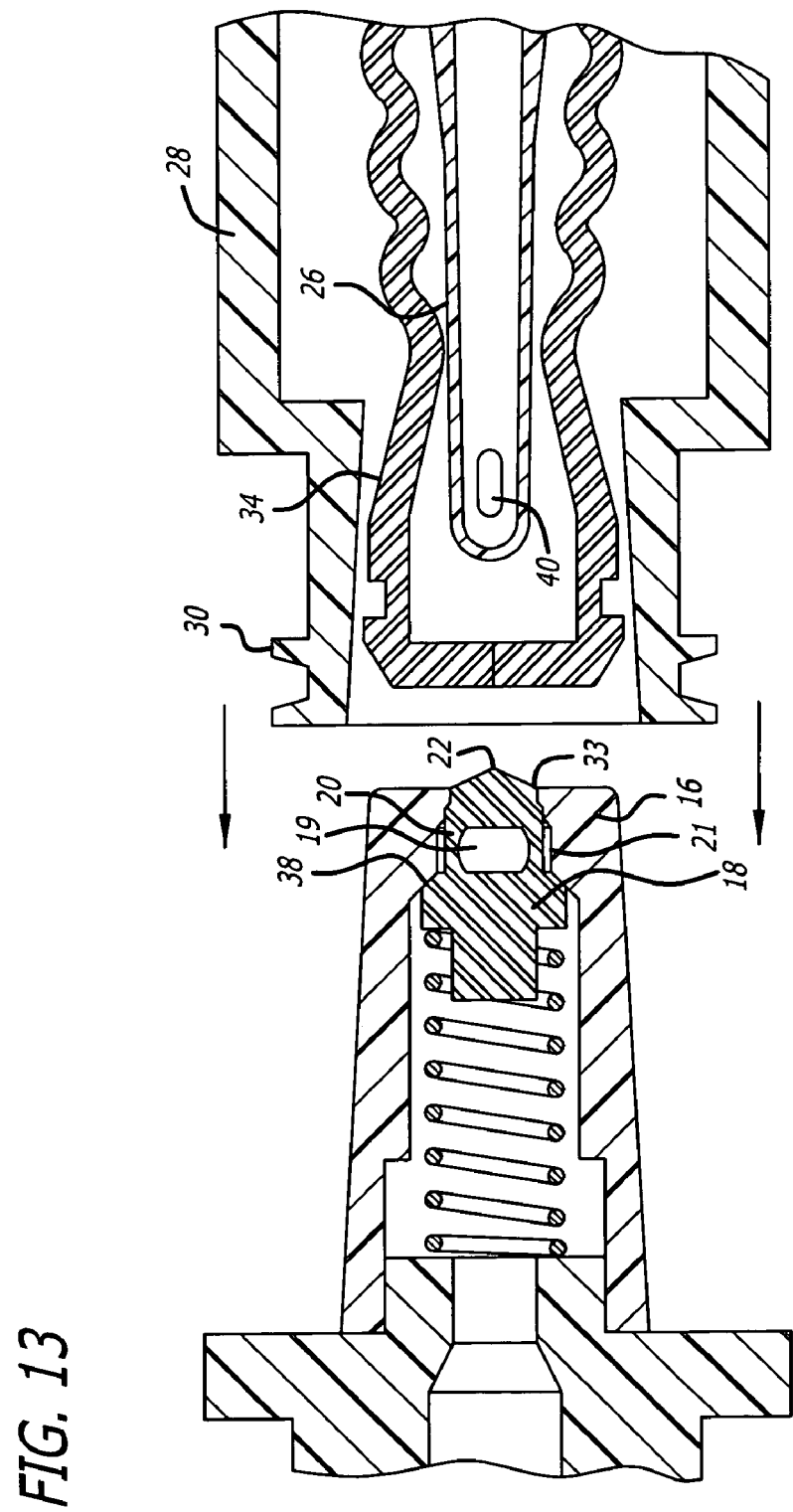
FIG. 13 is an illustration of a male luer valve that does not contain a housing element.

FIG. 13 is an illustration of a male luer valve that does not contain a housing element. This view is similar to FIG. 2 except that the male luer valve is not contained within a housing element and instead can be self-sustained. However, the function of the male luer valve is the same as that explained for FIG. 2 only that the engagement with the female luer housing does not occur with the male luer housing.

The various embodiments of the male luer described above provide for automatic sealing of the end opening in the male luer as the male and female luers are disconnected, reducing the risk of an operator coming into contact with the potentially hazardous fluid flowing through the connector.

Although some exemplary embodiments of the invention have been described above by way of example only, it will be understood by those skilled in the field that modifications may be made to the disclosed embodiments without departing from the scope of the invention, which is defined by the appended claims.

I claim:

1. A male luer medical fluid connector for engaging a female luer connector to open a flow channel through the male luer connector, the male luer connector comprising:
   a male luer portion having a forward end for engaging a female connector;
   a dual stage valve member located within the male luer portion, the valve member having an open position when the male luer portion is engaged with a female connector at which position fluid can flow through the male luer portion, and a closed position when the male luer portion is disengaged from a female connector at which position fluid is prevented from flowing through the male luer portion; and
   a vacuum section that creates a relative vacuum within the forward end of the male luer portion;
   wherein a first valve stage of the dual stage valve member is configured to isolate the vacuum section from upstream liquid before a second valve stage of the dual stage valve member closes.

2. The male luer medical fluid connector of claim 1 wherein the vacuum section is located between the first and second valve stages of the dual stage valve and is configured such that after the first valve stage closes, the vacuum section creates the relative vacuum thereby drawing liquid that may exist on the forward end into the forward end of the male luer portion before the second valve stage closes.

3. The male luer medical fluid connector of claim 2 wherein the vacuum section comprises a part of the valve element located between the first and second valve stages.

4. The male luer medical fluid connector of claim 3 wherein the vacuum section comprises a compressible cavity formed in the valve member, the cavity being compressed when the valve member is in the open position and the cavity being restored when the valve element is in the closed position.

5. The male luer medical fluid connector of claim 1 further comprising a resilient member that biases the valve member to the closed position.

* * * * *